United States Patent
Dietliker et al.

(10) Patent No.: US 6,770,420 B2
(45) Date of Patent: Aug. 3, 2004

(54) ALKYLSULFONYLOXIMES FOR HIGH-RESOLUTION I-LINE PHOTORESISTS OF HIGH SENSITIVITY

(75) Inventors: Kurt Dietliker, Fribourg (CH); Martin Kunz, Efringen-Kirchen (DE); Hitoshi Yamato, Hyogo (JP); Christoph De Leo, Ehrenkirchen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/612,800

(22) Filed: Jul. 2, 2003

(65) Prior Publication Data

US 2004/0013974 A1 Jan. 22, 2004

Related U.S. Application Data

(62) Division of application No. 09/242,145, filed as application No. PCT/EP97/04566 on Aug. 22, 1997, now abandoned.

(30) Foreign Application Priority Data

Sep. 2, 1996 (CH) .............................................. 2147/96

(51) Int. Cl.$^7$ ....................... G03F 7/004; C07C 255/00; C08F 2/46

(52) U.S. Cl. .................... 430/270.1; 430/325; 430/919; 430/921; 522/59; 522/57; 558/301; 568/30

(58) Field of Search ............................. 430/270.1, 325, 430/326, 919, 921; 522/57, 59; 558/301; 568/30

(56) References Cited

U.S. PATENT DOCUMENTS 6,017,675 A * 1/2000 Dietliker et al. ......... 430/270.1

* cited by examiner

Primary Examiner—Rosemary Ashton
(74) Attorney, Agent, or Firm—Kevin T. Mansfield

(57) ABSTRACT

The invention describes the use of oxime alkyl sulfonate compounds of formula 1

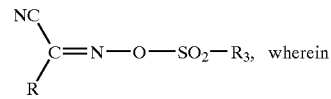

(1)

R is naphthyl, 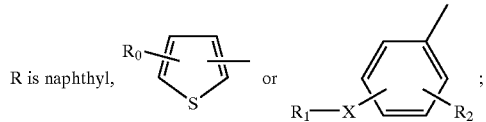

$R_0$ is either an $R_1$—X group or $R_2$;

X is a direct bond, an oxygen atom or a sulfur atom;

$R_1$ is hydrogen, $C_1$–$C_4$alkyl or a phenyl group which is unsubstituted or substituted by a substituent selected from the group consisting of chloro, bromo, $C_1$–$C_4$alkyl and $C_1$–$C_4$-alkyloxy;

$R_2$ is hydrogen or $C_1$–$C_4$alkyl; and $R_3$ is straight-chain or branched $C_1$–$C_{12}$alkyl which is unsubstituted or substituted by one or more than one halogen atom;

as photosensitive add generator in a chemically amplified photoresist which is developable in alkaline medium and which is sensitive to radiation at a wavelength of 340 to 390 nanometers and correspondingly composed positive and negative photoresists for the above-mentioned wavelength range.

14 Claims, No Drawings

ALKYLSULFONYLOXIMES FOR HIGH-RESOLUTION I-LINE PHOTORESISTS OF HIGH SENSITIVITY

This is a divisional of application Ser. No. 09/242,145 filed on Feb. 2, 1999, now abandoned which is a 371 of PCT/EP97/D4566 filed Aug. 22, 1997.

The present invention relates to specific oxime alkyl sulfonate compounds, i.e. compounds containing the structural unit

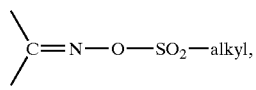

and to their use as photo-sensitive acid generator in chemically amplified photoresists, in printing plates, colour filters or image recording materials which are developable in alkaline medium, to their use as dissolution inhibitors in a corresponding positive photoresist, and to a process for the production of images using such resists, printing plates or image recording materials.

A chemically amplified photoresist will be understood as meaning a resist composition, the photosensitive component of which, when irradiated, generates only that amount of acid which is required to catalyse a chemical reaction of at least one acid-sensitive component of the resist, as a result of which the ultimate differences in solubility between irradiated and non-irradiated areas of the photoresist first develop.

Industrial paint formulations based on a large number of photosensitive oxime sulfonates and conventional acid-curable resins are disclosed in U.S. Pat. No. 4,540,598. These formulations are cured firstly with actinic light, especially with radiation in the range of 250 to 400 nanometers. The oxime sulfonates generate acid, so that a thermal cure in which the material also becomes insoluble in customary solvents is able to take place even at quite low temperatures. Nothing can be inferred about an imagewise exposure of corresponding resist films or about related problems as well as the image properties of the numerous formulations falling within the generic scope of the teaching of this patent specification. Oxime sulfonates, which are sparingly soluble in alkaline-aqueous developers, can be converted to the soluble form of the free acid by irradiation. Combined with a suitable film-forming resin, they can therefore be used as dissolution inhibitors for the production of positive resists.

Conventional positive photoresist compositions based on oxime sulfonates and alkali-soluble binders, typically cresol novolaks or hydroxymethacrylate/acrylic acid copolymers, are also known and are disclosed in EP-A-0 241 423. According to this reference, radiation of 200 to 600 nm can be used for exposing the resists. The shortcoming of these photo-resists is, however, that resolution and sensitivity are simultaneously never altogether satisfactory. This is particularly the case upon exposure to radiation in the range of the mercury i-line, which has a wavelength of 365 nanometers and is often used for the imagewise exposure of resist films, because mercury medium- and high-pressure lamps are inexpensive sources of radiation for producing radiation of these wavelengths with good intensity.

In the article "Photochemistry of Imino Sulfonate Compounds and Their Application to Chemically Amplified Resists" by Masamitsu Shirai and Masahiro Tsunooka; Journal of Photopolymer Science and Technology, Vol. 3(3), 1990, p. 301–304, there are also disclosed chemically amplified photoresist compositions based on oxime sulfonates as acid generator and poly(p-tert-butyloxycarbonyloxystyrene) as acid-sensitive component. The styrene component decomposes, catalysed by the acid generated by the acid generator upon exposure to irradiation to form poly(p-hydroxystyrene). This results in the exposed areas becoming soluble in alkaline developers so that positive images can be obtained with such developers. The described oxime sulfonates have an absorption maximum of about 250 nanometers in the UV/VIS spectrum, but have only low absorption for radiation in the wavelength of 313 nanometers and higher. Thus only a low sensitivity of the compositions to 313 nanometers radiation was found.

GB-A 2 306 958 describes the use of oxime sulfonates as photosensitive acid generators which are in particular suitable for use with light having a wavelength higher than 390 nm. However, the resolution and sensitivity of the resist formulations obtained with these initiators is not satisfactory.

Accordingly, there is still a need for reactive nonionic latent acid generators which are thermally and chemically stable and which, after being activated by light, in particular by radiation having the wavelength of the mercury i-line (365 nm), can be used as catalysts for different acid-catalysed reactions, such as polycondensation reactions, acid-catalysed depolymerisation reactions, acid-catalysed electrophilic substitution reactions or the acid-catalysed removal of protective groups. There is, in particular, a need for acid generators which can be activated with light and with which systems of higher sensivity and better resolution are obtained, having improved properties such as the form of the resist profiles and steepness of the side walls. Furthermore, there is a need for compounds which are converted to an acid when exposed to light and which can act as dissolution inhibitors in resist formulations.

U.S. Pat. No. 5,627,011 discloses the use of oxime sulfonate compounds in high-resolution i-line photoresists of high sensitivity. However, this publication only mentions oxime sulfonate compounds which can generate aromatic sulfonic acids. Surprisingly, it has now been found that resists of good sensitivity, resolution and having excellent resist profiles are obtained when an alkyl sulfonic acid is photochemically generated.

U.S. Pat. No. 4,451,286 discloses, among other oximes which do not contain any sulfonic acid groups, the compounds methylsulfonyloxyiminobenzylcyanide, methylsulfonyloxyiminonaphthylcyanide and methylsulfonyloxyimino-3-thiophenylcyanide in combination with chloroacetanilide compounds as plant protection agents.

This invention provides photoresist compositions having excellent resolution coupled with excellent sensitivity. These properties are observed especially when the resist compositions are exposed to radiation in the range of the mercury i-line which has a wavelength of about 365 nanometers.

Surprisingly, excellent resolution and outstanding sensitivity are achieved by using oxime alkyl sulfonates of formula I below which have been specially chosen with respect to the chromophoric part of the molecule as photo-acid generators in chemically amplified photo-resist compositions which are developable in aqueous-alkaline media. This applies both to corresponding negative as well as to positive photoresists containing an acid-sensitive component that undergoes an acid-catalysed chemical reaction which changes the solubility of the compositions in aqueous-alkaline developers.

Accordingly, this invention relates to compositions which can be actived by light, comprising a) at least one compound which may be crosslinked by the action of an acid and/or b) at least one compound which changes its solubility under the action of an acid, and c) as photoinitiator at least one compound of formula 1

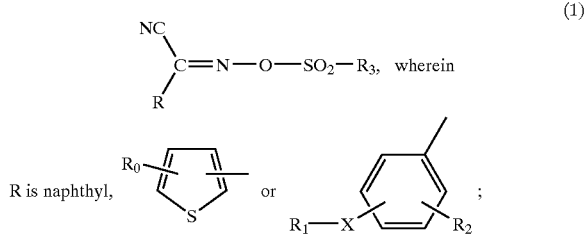

(1)

$R_0$ is either an $R_1$—X group or $R_2$;

X is a direct bond or an oxygen atom;

$R_1$ is hydrogen, $C_1$–$C_4$alkyl which is unsubstituted or substituted by phenyl, OH or $C_1$–$C_4$-alkoxy or which may be interrupted by an —O-atom, or $R_1$ is a phenyl group which is unsubstituted or substituted by a substituent selected from the group consisting of chloro, bromo, $C_1$–$C_4$alkyl and $C_1$–$C_4$alkyloxy;

$R_2$ is hydrogen or $C_1$–$C_4$alkyl; and $R_3$ is straight-chain or branched $C_1$–$C_{12}$alkyl, which is unsubstituted or substituted by one or more than one halogen atoms, or is phenyl-$C_1$–$C_2$alkyl or campheryl, which composition can contain other photoinitiators, sensitisers and/or additives besides component c). The invention also relates to the use of compounds of formula 1 as photosensitive acid generators in a photoresist sensitive to radiation in a wavelength of up to 390 nanometers.

The invention further relates to chemically amplified photoresists which are developable in alkaline medium and which are sensitive to radiation in the range from 340 to 390 nanometers, which resists are based on oxime alkyl sulfonates as photosensitive acid generator and contain a compound of formula 1 as defined above as oxime alkyl sulfonate.

According to this invention it is also possible to use mixtures of isomeric forms (cis-trans isomers, also known as E/Z- or syn/anti-isomers) of the oxime alkyl sulfonates of formula 1.

It is the object of this invention to provide, in particular, photoresists comprising compounds of formula 1. These resists encompass chemically amplified, positive photoresists which are developable in alkaline medium and are sensitive to radiation in the range from 340 to 390 nanometers, which resists are based on oxime alkyl sulfonates as photosensitive acid generator and contain a compound of the above formula 1 as oxime alkyl sulfonate, wherein X, R, $R_0$, $R_1$, $R_2$ and $R_3$ also have the meanings assigned to them above.

Another embodiment of the invention relates to chemically amplified, negative photoresists which are developable in alkaline medium and are sensitive to radiation in the range from 340 to 390 nanometers, which resists are based on oxime alkyl sulfonates as photosensitive acid generator and contain a compound of formula 1 defined above as oxime alkyl sulfonate, wherein R, $R_0$, $R_3$ and X have the meanings assigned to them above, and $R_1$ is hydrogen, $C_1$–$C_4$alkyl or a phenyl group which is unsubstituted or substituted by a substituent selected from the group consisting of chloro, bromo, $C_1$–$C_4$alkyl and $C_1$–$C_4$alkyloxy, and $R_2$ is hydrogen or $C_1$–$C_4$alkyl.

Both embodiments of the inventive photoresists are readily able to resolve structural units having dimensions in the submicron range, typically structures having dimensions down to 0.3 μm, the radiation used being in the range of c. 340 to 390 nanometersm. The resist structures remaining on the substrate after development exhibit in addition very good steepness of the side walls. The resists further have superior lithographic sensitivity to the given radiation. This feature was especially unexpected, as the oxime alkyl sulfonates chosen as acid generators absorb radiation of this wavelength only to an extremely low extent. The novel photoresists therefore match deep UV resists as regards lithographic properties, but have the advantage that they work with radiation of the near UV range with which it is possible to effect exposure technically very much easier.

The photoresists preferably comprise compounds of formula 1, wherein R is

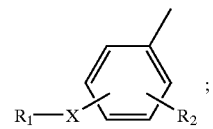

X is a direct bond or an oxygen atom; $R_1$ is $C_1$–$C_4$alkyl or phenyl; $R_3$ is straight-chain or branched $C_1$–$C_{12}$alkyl which is unsubstituted or substituted by one or more than one halogen atom.

This invention also relates to the use of compounds of formula 1 as photoinitiators for compounds which can be crosslinked by the action of an acid or/and as dissolution inhibitors for compounds which change their solubility under the action of an acid, where the irradiation is carried out, for example, imagewise.

Some of the compounds of formula 1 are novel. Accordingly, this invention also relates to compounds of formula 1a

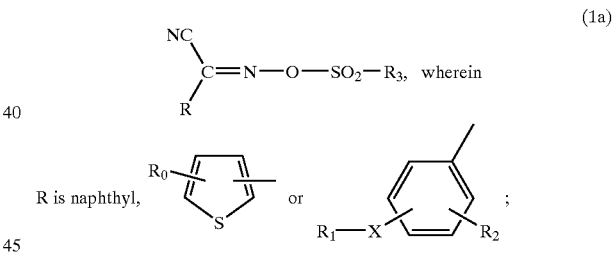

(1a)

$R_0$ is either a $R_1$—X group or $R_2$;

X is a direct bond, an oxygen atom or a sulfur atom;

$R_1$ is hydrogen, $C_1$–$C_4$alkyl or a phenyl group which is unsubstituted or substituted by a substituent selected from the group consisting of chloro, bromo, $C_1$–$C_4$alkyl and $C_1$–$C_4$alkyloxy;

$R_2$ is hydrogen or $C_1$–$C_4$alkyl; and $R_3$ is straight-chain or branched $C_1$–$C_{12}$alkyl which is unsubstituted or substituted by one or more than one halogen atom, with the proviso that, if $R_3$ is methyl, R is not naphthyl, phenyl or 3-thienyl.

$R_1$ and $R_2$ defined as $C_1$–$C_4$alkyl can be each independently of the other methyl, ethyl, n-propyl, i-propyl, n-butyl-, i-butyl, sec-butyl or tert-butyl.

$R_3$ defined as straight-chain or branched $C_1$–$C_{12}$alkyl can typically be methyl, ethyl, n-propyl, i-propyl, n-butyl-, i-butyl, sec-butyl, tert-butyl, n-octyl or n-dodecyl. If $C_1$–$C_{12}$alkyl $R_3$ is substituted by halogen, then it is, for example, chloromethyl, trichloromethyl, 3-chloropropyl, trifluoromethyl or completely fluorinated radicals derived from the cited alkyl radicals. Substituted by one or more than one halogen means, for example, substituted by one to three or two halogens, preferably by one to three halogens.

Preferred photoresists, printing plates, colour filters or image recording systems according to this invention comprise oxime alkyl sulfonate compounds of formula

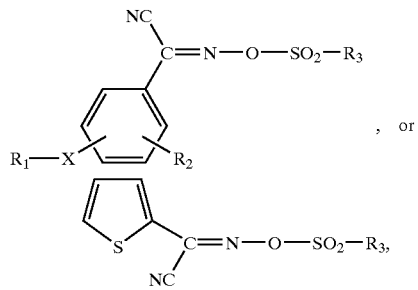

, or

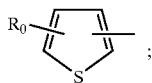

wherein

X is a direct bond or an oxygen atom, $R_1$ is hydrogen, phenyl or $C_1$–$C_4$alkyl, $R_2$ is hydrogen or $C_1$–$C_4$alkyl, and $R_3$ is straight-chain or branched $C_1$–$C_8$alkyl, trichloromethyl or trifluoro-methyl.

Of these, those photoresists are particularly preferred which comprise an oxime sulfonate compound, wherein X is a direct bond or an oxygen atom, $R_1$ is a $C_1$–$C_4$alkyl radical, preferably methyl or ethyl, or phenyl, and $R_2$ is hydrogen or methyl. Very particularly preferably, X is a direct bond or oxygen, $R_1$ is methyl, $R_2$ is a hydrogen atom or methyl, and $R_3$ is a $CH_3$, $CCl_3$ or $CF_3$ group.

Also preferred are photoresists based on compounds of formula 1 as acid generator, wherein R is

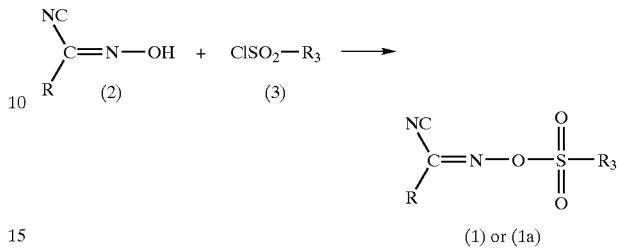

$R_0$ is hydrogen, and $R_3$ is straight-chain or branched $C_1$–$C_{12}$-alkyl which is unsubstituted or substituted by one or more than one halogen atom.

Preferred compounds are those of formula 1a, wherein X is a direct bond or an oxygen atom; $R_1$ is hydrogen or $C_1$–$C_4$alkyl, and $R_3$ is straight-chain or branched $C_1$–$C_8$alkyl which is unsubstituted or substituted by one or more than one halogen atom, or $CCl_3$ or $CF_3$.

Particularly interesting compounds are α-(methylsulfonyloxyimino)-4-methoxybenzylcyanide, α-(methylsulfonyloxyimino)-3-meth-oxybenzylcyanide, α-(methylsutfonyloxyimino)-4-methylbenzylcyanide, α-(methylsulfonyl-oxyimino)-3,4-dimethylbenzylcyanide, α-(methylsutfonyloxyimino)thiophene-3-acetonitrile , α-(methylsulfonyloxyimino)thiophene-2-acetonitrile, α-(isopropylsulfonyloxyimino)thiophene-2-acetonitrile, α-(butylsulfonyloxyimino)thiophene-2-acetonitrile, α-(octylsulfonyloxyimino)thio-phene-2-acetonitrile, α-(dodecylsulfonyloxyimino)thiophene-2-acetonitrile, α-(dodecylsulfonyloxyimino)thioph ne-2-acetonitrile, α-(3-chloropropylsulfonyloxyimino)thiophene-2-acetonitrile, α-(trifluorometyhlsulfonyloxyimino)thiophene-2-acetonitrile, α-(octylsulfonyloxyimino)-4-methoxybenzylcyanide, α-(3-chloropropylsulfonyloxyimino)-4-methoxybenzylcyanide. Mixtures of isomeric forms (cis/trans isomeres, also called E/Z- or syn/anti-isomers) are also novel.

The novel oxime alkyl sulfonates of formula 1 or 1a can be prepared by methods described in the literature, e.g. by reacting suitable free oximes of formula 2 with alkylsulfonic acid halides of formula 3 in the presence of a base such as triethylamine, or by reacting the salt of an oxime with an alkylsulfonic acid chloride. These methods have been published, inter alia, in EP-A 48615.

The reaction is conveniently carried out in an inert organic solvent in the presence of a tertiary amine.

The sodium salts of oximes can be obtained, for example, by reacting the corresponding oxime with a sodium alcoholate in dimethylformamide (DMF).

Oxime alkylsulfonic acid derivatives containing a heterocyclic aromatic five-ring substituent can also be prepared by 1,3-dipolar cycloaddition of suitable alkylsulfonic acid derivatives, typically the esters of oximinomalodinitrile or oximinocyanoacetate, with a suitable 1,3-dipolar compound, such as nitrile oxide. Such a synthesis is described, inter alia, in J. Perrocheau, R. Carré, Bull. Soc. Chim. Belge 1994, 103, 9.

The oxime alkyl sulfonates can be obtained in the syn- (E, cis) or anti- (Z, trans) form or also as mixtures of the two conformers. According to this invention it is possible to use single conformers as well as any mixture of the two conformers.

The oximes (2) required for the reaction can be prepared in general analogy to known methods, for example by reacting compounds containing reactive methylene groups, such as benzylcyanide derivatives or phenylacetic acid derivates, with an alkyl nitrite, e.g. methyl nitrite or isoamyl nitrite, and a sodium alcoholate, e.g. sodium methanolate. Such reactions are described, inter alia, in "The systematic identification of organic compounds", John Wiley and Sons, New York, 1980, p. 181, in "Die Makromolekulare Chemie", 1967, 108, 170, or in "Organic Synthesis", 1979, 59, 95.

Oximes can also be obtained e.g. by reacting a corresponding carbonyl compound or thiocarbonyl compound with hydroxylamine. They can also be prepared by the nitrosation of hydroxyaromatics.

The preparation of alkylsulfonic acid halides (3) is known to the skilled person and is described, for example, in the standard chemistry textbooks.

In photocurable compositions, oximesulfonic acid esters act as latent curing catalysts: when irradiated with light they generate acid which catalyses the crosslinking reaction. In addition, the acid generated by the radiation can, for example, catalyse the removal of suitable acid-sensitive protective groups from a polymer structure, or the cleavage of polymers containing acid-sensitive groups in the polymer backbone. Other applications are, for example, colour-change systems based on a change in the pH or in the solubility of, for example, a pigment protected by acid-sensitive protective groups. Finally, oximesulfonic acid esters that are sparingly soluble in an aqueous-alkaline developer can be rendered soluble in the developer by means of light-induced conversion into the free acid, with the result that they can be used as dissolution inhibitors in combination with suitable film-forming resins. Resins that can be crosslinked by acid catalysis are, for example, mixtures of polyfunctional alcohols or hydroxy-group-containing acrylic and polyester resins, or partially hydrolysed polyvinyl acetals or polyvinyl alcohols with polyfunctional acetal derivatives. Under certain conditions, for example the acid-catalysed self-condensation of acetal-functionalised resins is also possible. In addition, oximesulfonates can be used e.g. as hardeners which can be activated by light for siloxane group-containing resins. Those resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. This type of polycondensation of polysiloxanes is described, for example, in J. J. Lebrun, H. Pode, Comprehensive Polymer Science, Volume 5, page 593, Pergamon Press, Oxford, 1989.

As already mentioned above, the difference in solubility between irradiated and non-irradiated sections that occurs as a result of the acid-catalysed reaction of the resist material during or after irradiation of the resist may be of two types depending on which further constituents are present in the resist. If the compositions according to the invention comprise components that increase the solubility of the composition in the developer, the resist is positive. If, on the other hand, these components reduce the solubility of the composition, the resist is negative.

Acid-sensitive components that produce a negative resist characteristic are in particular compounds that, when catalysed by acid (the acid formed during irradiation of the compound of formula 1), are capable of undergoing a crosslinking reaction with themselves or with one or more further components of the composition. Compounds of this type are, for example, the known acid-curable resins, such as, for example, acrylic, polyester, alkyd, melamine, urea, epoxy and phenolic resins, or mixtures thereof. Amino resins, phenolic resins and epoxy resins are very suitable. Acid-curable resins of this type are generally known and are described, for example, in Ullmann's Encyclopädie der technischen Chemie, 4th Edition, Vol. 15 (1978), p. 613–628. They should generally be present in a concentration of 2 to 40% by weight, preferably of 5 to 30% by weight, based on the total solids content of the negative composition.

Very particularly preferred as acid-curable resins are amino resins, such as non-etherified or etherified melamine, urea, guanidine or biuret resins, preferably methylated melamine resins or butylated melamine resins, corresponding glycolurils and urones. Resins are understood in this context to be the customary technical mixtures, which usually also comprise oligomers, as well as pure and high purity compounds. N-methoxymethyl melamine (formula 7) and tetramethoxymethyl glucoril (formula 8) and N,N'-dimethoxymethylurone (formula 9) are the acid-curable resins given the greatest preference

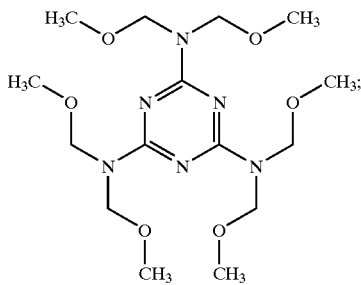

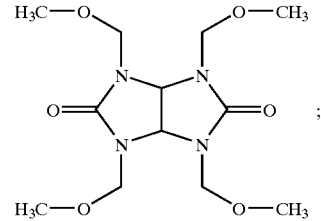

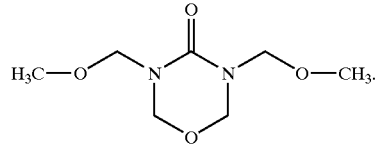

The concentration of the compound of formula I in negative resists is typically from 0.1 to 30% by weight, preferably up to 20% by weight, likewise based on the total solids content of the compositions. From 1 to 15% by weight is very particularly preferred.

Where appropriate, the negative compositions may additionally comprise a film-forming polymeric binder. This binder is preferably an alkali-soluble phenolic resin. Well suited for that purpose are, for example, novolaks, derived from an aldehyde, typically acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tert-butyl-phenol, p-nonylphenol, p-phenylphenol, resorcinol, bis(4-hydroxyphenyl)methane or 2,2-bis(4-hydroxyphenyl) propane. Also suitable are homo- and copolymers based on ethylenically unsaturated phenols, for example homopolymers of vinyl- and 1-propenyl-substituted phenols, such as p-vinylphenol or p-(1-propenyl)phenol, or copolymers of these phenols with one or more than one ethylenically unsaturated material, for example styrenes. The amount of binder should generally be from 30 to 95% by weight or, preferably, from 40 to 80% by weight.

The invention thus includes, as a special embodiment, negative photoresists which are developable in alkaline medium for a working radiation of a wavelength of more than 390 nanometers, comprising an oxime alkyl sulfonate of formula 1 as described above, an alkali-soluble phenolic resin as binder and a component that, when catalysed by an acid, undergoes a crosslinking reaction with itself and/or with the binder.

A particularly preferred form of that negative resist comprises from 1 to 15% by weight of oxime alkyl sulfonate, from 40 to 99% by weight of a phenolic resin as binder, for example one of those mentioned above, and from 0.5 to 30% by weight of a melamine resin as crosslinking agent, the percentages relating to the solids content of the composition. Using novolak or, in particular, polyvinyl phenol as binder gives a negative resist having especially good properties.

It is preferred to use a negative resist comprising N-methoxymethyl melamine or tetramethoxymethyl glucoril and N,N'-dimethoxymethylurone in high purity or technical form as amino resin.

Oximesulfonates can also be used as acid generators which can be photochemically activated for the acid-catalysed crosslinking of, for example, poly(glycidyl) methacrylates in negative resist systems. Such crosslinking reactions are described, inter alia, by Chae et al. in Pollimo 1993, 17(3), 292.

Monomeric or polymeric compounds that are alkali-insoluble but are cleaved in the presence of acid, or are capable of being rearranged intramolecularly, in such a manner that reaction products remain that are soluble in a customary alkaline developer and/or that cause an otherwise alkali-insoluble and acid-resistant additional binder to become soluble in the developer, also produce a positive characteristic in novel photoresist compositions. Substances of that type are referred to hereinafter as dissolution inhibitors.

The invention therefore includes, as a further special embodiment, positive photoresists developable in alkaline medium for a working radiation of a wavelength of 340 to 390 nanometers, comprising a compound of formula 1, and at least one compound that substantially prevents the composition from dissolving in an alkaline developer, but that can be cleaved in the presence of an acid in such a manner that reaction products remain that are soluble in the developer and/or that cause an acid-resistant additional binder that would otherwise be virtually insoluble in the developer to dissolve in the developer.

There may be used as dissolution inhibitors monomeric and polymeric organic compounds having functional groups that would be soluble per se in an alkaline medium, for example aromatic hydroxyl groups, carboxylic acid groups, secondary amino groups and keto or aldehyde groups, but that have been chemically so altered by reaction with a suitable compound that they are insoluble in aqueous alkali, the protective groups formed in the mentioned reaction being capable of being cleaved again by acid catalysis in such a manner that the functional groups are recovered in their original form.

For the protection of hydroxyl groups, carboxylic acid groups or secondary amino groups there are suitable, for example, dihydrofuran or 3,4-dihydropyran and the derivatives thereof, benzyl halides, alkyl halides, haloacetic acid, haloacetates, chlorocarbonates, alkylsulfonyl halides, aromatic sulfonyl halides, dialkyl dicarbonates or trialkylsilyl halides, it being possible for the reactions to be carried out in known manner. Customary conversion into ketals and acetals is suitable for protecting keto and aldehyde groups. Such chemically amplified positive resist systems are described, inter alia, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Compounds carrying blocked aromatic hydroxyl groups are particularly preferred, which compounds may likewise be monomers as well as polymers. The aromatic monomers preferably contain one or more than one aromatic nucleus, preferably 2 to 6 aromatic nuclei, containing 6 to 14, preferably 6, ring carbon atoms. In addition to containing the blocked hydroxyl groups, the aromatic nuclei may of course contain further substituents, preferably $C_1$–$C_4$alkyl, $C_1$–$C_4$alkoxy or halogen. Particularly preferred monomeric dissolution inhibitors are bisphenyl types, i.e. compounds of formula

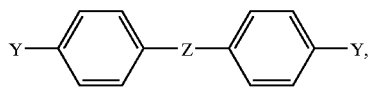

wherein each Y is an acid-sensitive group, such as a phenolic hydroxyl group, which is protected by a suitable acid-sensitive radical such as the ether, carbonate, silyl, tetrahydropyranyl or tetrahydrofuranyl groups (se e.g. EP-A 475903), and Z is either a direct single bond or may be one of the following groups: —S—; —O—; —SO—; —SO$_2$—; —CO—; —C($R_a$)($R_b$)—, where $R_a$ may be hydrogen, methyl or aryl, and $R_b$ may be hydrogen or methyl. Particularly preferred divalent radicals —C($R_a$)($R_b$)— are —CH$_2$—; —C(CH$_3$)$_2$— and C(CH$_3$)(Ph)—. The preferred polymeric dissolution inhibitors are derived from customary phenolic resins, typically from polyvinyl phenols, the hydroxyl groups of which are also blocked in a manner consistent with the above description. Dissolution inhibitors carrying protective groups of the indicated kind are known in the art. Inhibitors carrying carbonate groups are described, inter alia, by Dennis R. McKean, Scott A. McDonald, Nicholas J. Clecak and C. Grant Willson in "Novolac based deep-UV resists", SPIE Vol. 920 Advances in Resist Technology and Processing V (1988), p. 60–63, or by Masamitsu Shirai and Masahiro Tsunooka in "Photochemistry of Imino Sulfonate Compounds and their Application to Chemically Amplified Resists", Journal of Photopolymer Science and Technology, Vol. 3(3), 1990, p. 301–304. They can be prepared by standard known methods, for example as described by J. M. J. Frechet, E. Eichler, H. Ito and C. G. Willson, Polymer 24 (1983), p. 995. Dissolution inhibitors carrying trialkylsilyloxy or tert-butyloxy groups are disclosed in EP-A-0 329 610, inhibitors carrying protective groups of the tetrahydrofuranyl and tetrahydropyranyl type group are described, inter alia, by N. Hayashi, S. M. A. Hesp, T. Ueno, M. Toriumi, T. Iwayanagi and S. Nonogaki in Polym. Mat. Sci. Eng. 61 (1989), p. 417–421, and aromatic compounds carrying substituted tetrahydropyranyl groups are described in more detail in EP-A-0 475 903. The protective groups can be obtained in known manner by addition of 3,4-dihydropyrans or 3,4-dihydrofurans under acid conditions.

In positive resists of the mentioned type a film-forming polymeric dissolution inhibitor can either be the only binder in the photoresist or can be used in admixture with an acid-inert binder and, where appropriate, a monomeric dissolution inhibitor.

Examples of acid-inert binders are novolaks, especially those based on o-, m- or p-cresol and formaldehyde, also poly(p-hydroxystyrene), poly(p-hydroxy-α-methylstyrene) and copolymers of p-hydroxystyrene, p-hydroxy-α-methylstyrene and acetoxystyrene.

Examples of polymeric dissolution inhibitors are novolaks, especially those based on o-, m- or p-cresol and formaldehyde, poly(p-hydroxystyrene), poly(p-hydroxy-α-methylstyrene), copolymers of p-hydroxystyrene or p-hydroxy-α-methylstyrene and acetoxystyrene or acrylic acid and/or methacrylic acid and also (meth)acrylic acid esters, which are reacted in known manner with dihydrofuran, 3,4-dihydropyran, benzyl halides, alkyl halides, haloacetic acid, haloacetates, chlorocarbonates, alkylsulfonyl halides, aromatic sulfonyl halides, dialkyl dicarbonate or trialkylsilyl halides. Also suitable are polymers of p-(2-tetrahydropyranyl)oxy-styrene or p-(tert-butyloxycarbonyl)oxystyrene with (meth)acrylic acid, (meth)acrylates and/or p-acetoxystyrene and polymers of p-hydroxystyrene and/or p-(2-tetrahydropyranyl)-oxystyrene with 3-hydroxybenzyl (meth)acrylates, which can, if necessary, additionally be protected by reaction with one of the compounds listed above.

Particularly suitable are polymers that are transparent over a wavelength range from 180 to 1000 nm and which carry groups that, after acid-catalysed deprotecting, bring about a change in solubility, as well as hydrophobic and hydrophilic groups that increase the solubility of the acid generator and ensure aqueous-alkaline developability. Examples of such polymers are acrylates and methacrylates prepared by co- or ter-polymerisation from the corresponding monomers. The monomers may also carry organosilicon radicals in order, for example, to increase the resistance in the case of dry etching processes. Examples of monomers are: methyl (meth)acrylate, (meth)acrylic acid, tert-butyl (meth)acrylate, trimethylsilylmethyl (meth)acrylate, 3-oxocyclohexyl (meth)acrylate, tetrahydropyranyl (meth)acrylate, adamantyl (meth)acrylate, cyclohexyl (meth)acrylate, norbornyl (meth)acrylate.

The invention accordingly also relates to a chemically amplified positive resist comprising as photosensitive acid generator a compound of formula 1 as well as to a photoresist comprising polymers that are transparent up to the wavelength region of 180 nm.

A special embodiment of the positive resist according to the invention comprises from 75 to 99.5% by weight of a film-forming polymer that contains protective groups that can be removed by acid catalysis, and from 0.5 to 25% by weight of oxime alkyl sulfonates of formula 1, the percentages being based on the solids content of the compositions. In this context, preference is given to compositions comprising from 80 to 99% by weight of the mentioned polymer and from 1 to 20% by weight of oxime alkyl sulfonate.

Another embodiment is a positive resist comprising from 40 to 90% by weight of an acid-inert film-forming polymer as binder, from 5 to 40% by weight of a monomeric or polymeric compound having protective groups removable by acid catalysis, and from 0.5 to 25% by weight of oxime alkyl sulfonates of formula I, the percentages relating to the solids content of the compositions. Of those compositions, preference is given to those comprising from 50 to 85% by weight of acid-inert binder, from 10 to 30% by weight of monomeric or polymeric dissolution inhibitor and from 1 to 15% by weight of oxime alkyl sulfonates.

Oxime sulfonates can also be used as solubilisers which can be activated by light. In that case, the compounds are added to a film-forming material comprising substantially no components that polymerise with the oximesulfonate when heated or when irradiated with actinic radiation. However, the oximesulfonates reduce the speed at which the film-forming material dissolves in a suitable developer medium. This inhibiting effect can be cancelled by irradiating the mixture with actinic radiation, so that a positive image can be produced. Such an application is described, inter alia, in EP-A-241 423.

A further special embodiment of the invention is, finally, a positive resist comprising a compound of formula 1 and a binder that is virtually insoluble in an alkaline developer and that becomes soluble in the developer in the presence of the photolysis products of the compound of formula I. In this case the amount of the mentioned oximesulfonate compound is generally from 5 to 50% by weight, based on the solids content of the composition.

The use of the oxime alkyl sulfonates according to the invention in chemically amplified systems, which operates on the principle of the removal of a protective group from a polymer, generally produces a positive resist. Positive resists are preferred to negative resists in many applications, especially because of their greater resolution. There is, however, also interest in producing a negative image using the positive resist mechanism, in order to combine the advantages of the high degree of resolution of the positive resist with the properties of the negative resist. That can be achieved by introducing a so-called image-reversal step as described, for example, in EP-A-361 906. For that purpose, the image-wise irradiated resist material is treated, before the developing step, with e.g. a gaseous base, the acid that has been produced image-wise being neutralised. Subsequently, a second irradiation, over its whole area, and thermal after-treatment are carried out and the negative image is then developed in the customary manner.

In addition to the cited components, it is also possible to add compounds which accelerate or amplify the acid formation to the negative as well as to the positive photoresist compositions containing the novel oxime alkyl sulfonate. Such acid amplifiers are described, inter alia, in K. Arimitsu et al., J. photopolym. Sci Technol. 1995, 8, pp. 43, K. Kudo et al., J. photopolym. Sci Technol. 1995, 8, pp. 45, or K. Ichimura et al. Chem. Lett. 1995, pp. 551.

In addition to the mentioned constituents, both the negative and the positive photoresist compositions may additionally comprise one or more of the additives customarily used in photoresists in the amounts familiar to a person skilled in the art, for example flow control agents, wetting agents, adhesives, thixotropic agents, colourants, pigments, fillers, dissolution accelerators and so on. However, substances which additionally sensitise the compositions for the working irradation in the range of the mercury i-line should not be added because this would normally result in a reduced resolution of the resist. Typical examples of sensitisers which can be used in the novel composition in addition to component c) are, in particular, aromatic carbonyl compounds such as benzophenone, xanthone, thioxanthone, anthraquinone and 3-acylcoumarine derivatives as well as 3-(aroyl-methylene)thiazolines, and also eosine, rhodamine and erythrosine colourants.

For certain purposes, resin mixtures having monomeric or oligomeric constituents containing polymerisable unsaturated groups are used. Such surface coatings can also be cured using the compounds of formula 1. In addition to component c), it is possible to use 1. radical polymerisation initiators or 2. photoinitiators. The former initiate the polymerisation of the unsaturated groups during heat treatment, the latter during UV radiation. Examples of additional photoinitiators for use in the inventive compositions are, for example, radical photoinitiators, typically those from the class of the benzophenones, acetophenone derivatives, such as α-hydroxycycloalkylphenyl ketone, dialkoxyacetophenone, α-hydroxy- or α-aminoacetophenone, 4-aroyl-1,3-dioxolane, benzoin alkyl ethers and benzil ketals, monoacylphosphine oxides, bisacylphosphine oxides or titanocenes. Illustrative examples of particularly suitable additional photoinitiators are: 1-(4-dodecylbenzoyl)-1-hydroxy-1-methylethane, 1-(4-isopropylbenzoyl)-1-hydroxy-1-methyl-ethane, 1-benzoyl-1-hydroxy-1-methylethane, 1-[4(2-hydroxyethoxy)benzoy]-1-hydroxy-1-methylethan, 1-[4(acrylolyoxyethoxy)benzoyl]-1-hydroxy-1-methylethane, diphenyl ketone, phenyl-1-hydroxycyclohexyl ketone, (4-morpholinobenzoyl)-1-benzyl-1-dimethylaminopropane, 1-(3,4-dimethoxyphenyl)-2-benzyl-2-dimethylaminobutan-1-one, (4-methylthiobenzoyl)-1-methyl-1-morpholinoethane, benzil dimethyl ketal, bis(cyclopentadienyl)-bis(2,6-difluoro-3-pyrrylphenyl)titanium, trimethylbenzoyidiphenylphosphine oxide, bis(2,6-dimethoxybenzoyl)-(2,4,4-trimethyl-pentyl)phosphine oxide, bis(2,4,6-trimethylbenzoyl)-2,4-dipentoxyphenylphosphine oxide or bis(2,4,6-trimethylbenzoyl)phenylphosphine oxide. Other suitable additional photoinitiators are to be found in U.S. Pat. No. 4,950,581, column 20, line 35 to column 21, line 35. Other examples are trihalomethyltriazine derivatives or hexaarylbisimidazolyl compounds.

Further examples of additional photoinitiators are, for example, also cationic photoinitiators, typically peroxide compounds, such as benzoylperoxide (other suitable peroxides are described in U.S. Pat. No. 4,950,581, column 19, lines 17–25), aromatic sulfonium salts or iodonium salts, such as those to be found, inter alia in U.S. Pat. 4,950,581, column 18, line 60 to column 19, line 10, or cyclopentadienyl-arene-iron(II)-complex salts, typically ($\eta^6$-isopropylbenzol)($\eta^5$-cyclopentadienyl)-iron-II-hexafluorophosphate.

For application, the compositions must generally also comprise a solvent. Examples of suitable solvents are ethyl acetate, 3-methoxymethyl propionate, ethyl pyruvate, 2-heptanone, diethyl glycol dimethyl ether, cyclopentanone, cyclohexanone, γ-butyrolactone, ethyl methyl ketone, 2-ethoxyethanol, 2-ethoxyethyl acetate and, in particular, 1-methoxy-2-propyl acetate. The solvent may also be in the form a mixture, for example of two or more of the above-mentioned solvents. The choice of solvent and the concentration depend, for example, on the nature of the composition and on the coating method.

The solution is uniformly applied to a substrate by means of known coating methods, for example by spin-coating, immersion, knife coating, curtain coating techniques, brush application, spraying and reverse roller coating. It is also possible to apply the photosensitive layer to a temporary, flexible support and then to coat the final substrate by coating transfer (laminating).

The amount applied (coating thickness) and the nature of the substrate (coating substrat) are dependent on the desired field of application. The range of coating thicknesses can in principle include values from approximately 0.1 μm to more than 100 μm.

Possible areas of use of the composition according to the invention are as follows: use as photoresists for electronics, such as etching resists, electroplating resists or solder resists, the manufacture of integrated circuits or thin film transistor resist (TFT resist), the manufacture of printing plates, such as offset printing plates or screen printing templates, use in the etching of mouldings or in stereolithography techniques, use in colour filters or image recording materials and, preferably, use as microresist in the manufacture of integrated circuits. The coating substrates and processing conditions vary accordingly.

When using the compositions as microresists for integrated and large-scale integrated circuits, as preferred, the layer thicknesses are typically from 0.1 to 10 μm, preferably from 0.5 to 5 μm, most preferably from 0.5 to 1.5 μm. When using the compositions in resists for e.g. ion implantation the coating thicknesses are typically from 0.1 to 10 μm, preferably from 4 to 8 μm. By choosing suitable substituents $R_1$ and $R_2$, the optical density of the resist can be adjusted such that in particular the large layer thicknesses are also satisfactorily cured.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

After the coating operation, the solvent is generally removed by heating, resulting in a lay r of the photoresist on the substrate. The drying temperature must of course be lower than the temperature at which certain components of the resist might be thermally cured. Care must be taken in that respect especially in the case of negative photoresists. In general, drying temperatures should not exceed from 80 to 130° C.

The resist coating is then irradiated image-wise. This irradiation in a predetermined pattern using actinic radiation includes both irradiation through a photomask containing a predetermined pattern, for example a diapositive, and irradiation using a laser beam that is moved over the surface of the coated substrate, for example under the control of a computer, and thus produces an image.

Suitable radiation sources are those which emit radiation of a wavelength of approximately from 180 to 390, for example from about 340 to 360 or, preferably, from 360 to 390, nanometers. Both point sources and planiform projectors (arrays of reflector lamps) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. Particularly suitable are mercury vapour lamps, especially mercury medium- and high-pressure lamps, from whose radiation the emission lines at other wavelengths are filtered out, if required. This is the case in particular for short-wave radiation. The distance between the lamp and the substrate according to the invention to be irradiated can vary, for example, from 2 cm to 150 cm, according to the intended use and the type and/or strength of the lamp. A suitable laser-beam source is, for example, the argon-ion laser, which emits radiation at wavelengths of 364 and 388 nanometers. With that type of irradiation, it is not absolutely essential to use a photomask in contact with the photopolymeric coating; the controlled laser beam is capable of writing directly onto the coating. For that purpose the high sensitivity of the materials according to the invention is very advantageous, allowing high writing speeds at relatively low intensities. On irradiation, the oxime alkyl sulfonate in the composition in the irradiated sections of the surface coating decomposes to form sulfonic acids.

After the irradiation and, if necessary, thermal treatment, the unirradiated sites (in the case of positive resists) or the irradiated sites (in the case of negative resists) of the composition are removed in a manner known per se using a developer.

It is generally necessary to allow a certain period of time prior to the developing step in order to allow the acid-sensitive components of the resist composition to react. In order to accelerate that reaction and hence the development of a sufficient difference in solubility between the irradiated and unirradiated sections of the resist coating in the developer, the coating is preferably heated before being developed. The heating can also be carried out or begun during the irradiation. Temperatures from 60 to 150° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may be used, for example, for the developing. Such developers comprise, for example, sodium or potassium hydroxide, the corresponding carbonates, acid carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethyl ammonium hydroxide. The developer solutions are generally up to 0.5N, but are usually diluted in suitable manner before use. For example solutions having a normality of approximately 0.1 are well suited. The choice of developer depends on the nature of the photoresist, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of those solvents. A typical aqueous/organic developer system is based on butylcellosolve®/water.

Accordingly, this invention also relates to a process for the production of an image, which comprises coating a substrate with a composition according to this invention, irradiating the coating with radiation having a wavelength of 340 to 390 nanometers in a desired pattern and, after a heating period, removing the more soluble sections of the coating with an aqueous-alkaline developer.

In another of its aspects, this invention also relates to the use of the novel composition for the production of printing plates, colour filters, resist materials and image recording material, as well as to the use of componds of formula 1 or 1a as photosensitive acid generator sensitive to radiation at a wavelength of below 390 nm in the production of printing plates, colour filters, resist materials or image recording materials, or for image recording materials for holographic images.

It is known from EP-A-592 139 that oximesulfonates can be used as acid generators which can be activated by light in compositions that are suitable for the surface treatment and cleaning of glass, aluminium and steel surfaces. The use of these compounds in such organosilane systems results in compositions that have significantly better storage stability than those obtained when the free acid is used. Oximesulfonates can also be used to produce so-called "print-out" images when the compound is used together with a colourant that changes colour when the pH changes, as described in Japanese Patent Application JP-A Hei 4 328 552 or in U.S. Pat. No. 5,237,059. Such colour-change systems can be used according to EP-A-199 672 also to monitor goods that are sensitive to heat or radiation.

In addition to a colour change, it is possible during the acid-catalysed deprotection of soluble pigment molecules for the pigment crystals to be precipitated; this can be used in the production of colour filters.

The compounds of formula 1 are normally added to the compositions which can be activated by light in an amount of 0.1 to 30% by weight, e.g. of 0.5 to 10% by weight, preferably of 1 to 5% by weight.

The following Examples illustrate the invention in more detail. As in the remainder of the description and in the patent claims, parts and percentages are by weight, unless otherwise stated.

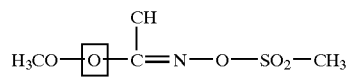

EXAMPLE 1

Preparation of α-hydroxyimino-4-methoxybenzylcyanide and α-(methylsulfonyl-oxyimino)-4-methoxybenzylcyanide 1.1. α-Hydroxyimino-4-methoxybenzylcyanide 64.5 g of methanol, 365 g of xylene and 80 g of sodium hydroxide (2 mol) are placed in a reactor together with 147 g (1 mol) of 4-methoxyphenylacetonitrile. Then 125 g (1.07 mol) of isopentyl nitrite are added dropwise at 40° C. over 2 hours. The reaction mixture is stirred first for 2 hours at this temperature and then for another 20 hours at room temperature.

Afterwards the reaction mixture is diluted with water to form an emulsion and the pH is adjusted to 14 with aqueous sodium hydroxide and the organic phase then is separated. The aqueous phase is acidified with hydrochloric acid and the product is extracted with ether. The ether phase is dried and the ether is stripped off. Recrystallisation from toluene gives 142 g of α-hydroxyimino-4-methoxybenzylcyanide, corresponding to a yield of 80.6% of theory. The $^1$H-NMR spectrum (acetone-$d_6$) shows two symmetrical multiplets in the aromatic range at 7.06 and 7.72 ppm (4 H), one singulet at 3.87 ppm (3 H) and one singulet at 12.37 ppm (1 H).

1.2. α-(Methylsulfonyloxyimino)-4-methoxybenzylcyanide 20 g (0.114 mol) of α-hydroxyimino-4-methoxybenzylcyanide are dissolved in 100 ml of tetrahydrofuran (THF) and charged with 17.2 g (0.17 mol) of triethylamine. To this mixture are added dropwise and with cooling 14.3 g (0.0.12 mol) of methanesulfonyl chloride dissolved in 50 ml of THF. This mixture is then warmed to room temperature and stirred for 12 hours. Subsequently, the reaction solution is diluted with 300 ml of $CH_2Cl_2$, washed with water, dilute hydrochloric acid and again with water and is then dried over magnesium sulfate. After filtration, the solvent is distilled off on a rotary evaporator and the brownish crude product is recrystallised from toluene, giving 23.9 g (83%) of α-(methyl-sulfonyloxy-imino)-4-methoxybenzylcyanide in the form of beige crystals having an m.p. of 124–125° C. The $^1$H-NMR spectrum of the compound shows the product to be a pure stereoisomer.

Elemental analysis: $C_{10}H_{10}N_2O_4S$ (254.25)

|         | C [%] | H [%] | N [%] | S [%] |
|---------|-------|-------|-------|-------|
| calcd.: | 47.24 | 3.96  | 11.02 | 12.61 |
| found:  | 47.25 | 3.90  | 10.97 | 12.65 |

EXAMPLE 2

α-(Methylsulfonyloxyimino)-3-methoxybenzylcyanide

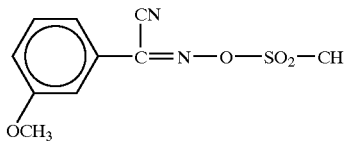

2.1. α-Hydroxyimino-3-methoxybenzylcyanide

α-Hydroxyimino-3-methoxybenzylcyanide prepared in general analogy to the method described under 1.1, using 3-methoxybenzylcyanide instead of 4-methoxybenzylcyanide as starting material and gaseous methyl nitrite (prepared according to Org. Synthesis 59, 95 (1979)) instead of the isopentyl nitrite. α-Hydroxyimino-3-methoxybenzylcyanide is obtained in a 45% yield as a colourless powder having an m.p. of 86–87° C. The $^1$H-NMR spectrum (CDCl$_3$) is consistent with the proposed structure: 8.84 (s, OH); 7.35–7.25 (m, 3 aromatic H); 7.05 (m, 1 aromatic H); 3.84 (s, CH$_3$O).

2.2. α-(Methylsulfonyloxyimino)-3-methoxybenzylcyanide

In general analogy to the process described under 1.2, 27.7 g (0.157 mol) of α-hydroxyimino-3-methoxybenzylcyanide are reacted in the presence of 23.9 g (0.236 mol) of triethylamine with 19.8 g (0.173 mol) of methanesulfonyl chloride. Recrystallisation from toluene gives 19.1 g (48%) of α-(methylsulfonyloxyimino)-3-methoxybenzylcyanide in the form of white crystals having an m.p. of 105–107° C.

Elemental analysis: C$_{10}$H$_{10}$N$_2$O$_4$S (254.25)

|         | C [%] | H [%] | N [%] | S [%] |
|---------|-------|-------|-------|-------|
| calcd.: | 47.24 | 3.96  | 11.02 | 12.61 |
| found:  | 47.45 | 4.01  | 11.42 | 12.64 |

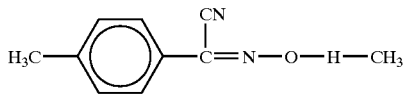

EXAMPLE 3

Preparation of α-(methylsulfonyloxyimino)-4methylbenzylcyanide

3.1 α-Hydroxyimino-4-methylbenzylcyanide 131.2 g (1 mol) of p-tolylacetonitrile are placed in a sulfonation flask and charged with 40 g (1 mol) of sodium hydroxide, dissolved in 325 ml of methanol. This solution is cooled in an ice bath to 0–5° C. At this temperature, 1 mol of gaseous methyl nitrite (prepared in situ by addition of 31.5 ml of conc. H$_2$SO$_4$, dissolved in 65 ml of water, to a solution of 83 g of NaNO$_2$ in 50 ml of water and 53 ml of methanol (see Org. Synthesis 1979, 59, 95)) is introduced, with stirring, over 3 hours. The ice bath is then removed and the red solution is stirred overnight at room temperature. The methanol is distilled off on a rotary evaporator and the orange residue is then charged with water and toluene. The aqueous phase is separated, washed twice with toluene and acidified with conc. HCl. The resulting orange emulsion is extracted three times with ethyl acetate, the extracts are washed with water and dried over magnesium sulfate. After filtration, the solvent is distilled off and a yellowish-orange oil is obtained which solidifies upon standing. Recrystallisation from toluene gives 133.6 g (83% of theory) of α-hydroxyimino-4-methylbenzylcyanide as a beige solid having a melting point of 110.5–114.5° C. The $^1$H-NMR spectrum is consistent with the proposed structure.

3.2 α-(Methylsulfonyloxyimino)-4-methylbenzylcyanide 33.6 g (0.21 mol) of α-hydroxyimino-4-methylbenzylcyanide and 31.9 g (0.31 mol) of triethylamine are dissolved in 425 ml of tetrahydrofuran and to this solution is then added dropwise a solution of 26.44 g (0.23 mol) of methanesulfonyl chloride at 0–5° C. After the addition is complete, the mixture is stirred for 30 minutes at 0° C. and then overnight at room temperature. Subsequently, the reaction mixture is filtered and the filtrate is washed with a saturated sodium chloride solution and dried over magnesium sulfate. The solvent is then distilled off on a rotary evaporator, giving a solid residue which is recrystallised from toluene. 37.3 g (75%) of α-(methylsulfonyloxyimino)-4-methylbenzylcyanide are obtained in the form of a colourless powder having an m.p. of 97.5–102.5° C. The $^1$H-NMR spectrum shows it to be a pure stereoisomer.

Elemental analysis: C$_{10}$H$_{10}$N$_2$O$_3$S (238.26)

|         | C [%] | H [%] | N [%] | S [%] |
|---------|-------|-------|-------|-------|
| calcd.: | 50.41 | 4.23  | 11.76 | 13.46 |
| found:  | 50.47 | 4.34  | 11.92 | 13.56 |

EXAMPLE 4

Preparation of α-(methylsulfonyloxyimino)-3,4-dimethylbenzylcyanide

4.1 α-Hydroxyimino-3,4-dimethylbenzylcyanide

In a sulfonation flask, 37.6 g (0.26 mol) of 3,4-dimethylacetonitrile are reacted with 0.52 mol of gaseous methyl nitrite, as described under 3.1. After the customary isolation, 23.2 g (50%) of α-hydroxyimino-3,4-dimethylbenzylcyanide are obtained as a brown resin. This crude product is used in the next step without any further purification. The $^1$H-NMR spectrum is consistent with the proposed structure.

4.2 α-(Methylsulfonyloxyimino)-3,4dimethylbenzylcyanide 23.2 g (0.13 mol) of α-hydroxyimino-3,4-dimethylbenzylcyanide are reacted with 27.2 ml (0.20 mol) of triethylamine and 11.1 ml (0.14 mol) of methansulfonyl chloride in tetrahydrofuran, as described under 3.2. After the usual processing, 32.6 g of a crude product are obtained, which is then recrystallised from isopropanol, giving 30.5 g (93%) of α-(methyl-sulfonyloxyimino)-3,4-dimethylbenzylcyanide in the form of a brownish powder having an m.p. of 91–95° C.

EXAMPLE 5

Preparation of α-(methylsulfonyloxyimino) thiophene-3-acetonitrile

5.1. α-Hydroxyiminothiophene-3-acetonitrile

In general analogy to the process described under 3.1, 59 g (0.48 mol) of thiophene-3-acetonitril are placed in a sulfonation flask and are charged with 19.2 g (0.48 mol) of sodium hydroxide, dissolved in 200 ml of methanol. 0.48 mol of gaseous methyl nitrite is introduced, with stirring, into this solution at 0–5° C. over 4.5 hours. The ice bath is then removed and the brown solution is stirred overnight at room temperature. The methanol is distilled off on a rotary evaporator and the resulting orange residue is charged with water and ethyl acetate. The aqueous phase is separated, washed twice with ethyl acetate and acidified with conc. HCl. The aqueous phase is extracted twice with ethyl acetate, the extracts are washed with water and dried over magnesium sulfate. After fitration, the solvent is distilled off and a brown solid is obtained which is then recrystallised from toluene, giving 28.6 g (39% of theory) of α-hydroxyiminothiophene-3-acetonitrile as a beige solid having a melting point of 96–106° C. The $^1$H-NMR spectrum is consistent with the proposed structure.

5.2 α-(Methylsulfonyloxyimino)thiophene-3-acetonitrile

In general analogy to the reaction described under 3.2, 15.2 g (0.1 mol) of α-hydroxyimino-thiophene-3-acetonitrile and 15.2 g (0.15 mol) of triethylamine are dissolved in 150 ml of tetrahydrofuran and to this is added dropwise a solution of 12.6 g (0.11 mol) of methanesulfonyl chloride at 0–5° C. After the addition is complete, the mixture is stirred for 30 minutes at 0° C. and then overnight at room temperature. The reaction mixture is filtered, the filtrate is washed with dilute hydrochloric acid and with saturated sodium chloride solution and then dried over magnesium sulfate. The solvent is distilled off on a rotary evaporator, giving a solid residue which is then recrystallised from ethyl acetate/hexane (2:1). 11.2 g (49%) of α-(methylsulfonyloxyimino)thiophene3-acetonitrile are obtained in the form of a colourless powder having an m.p. of 116–124° C. The $^1$H-NMR spectrum shows it to be the pure cis-isomer (Example 5a).

Elemental analysis: $C_7H_6N_2O_3S_2$ (230.26)

|  | C [%] | H [%] | N [%] | S [%] |
|---|---|---|---|---|
| calcd.: | 36.51 | 2.63 | 12.17 | 27.85 |
| found: | 36.58 | 2.54 | 11.92 | 28.70 |

The mother liquor is concentrated, affording a further 3.0 g (13%) of a colourless solid having an m.p. of 105–112° C. The $^1$H-NMR spectrum shows it to be a 80:20 mixture of the trans- and cis-isomers of α-(methylsulfonyloxyimino)thiophene-3-acetonitrile (Example 5b).

EXAMPLE 6

Preparation of α-(methylsulfonyloxyimino)thiophene-2-acetonitrile 6.1 α-Hydroxyiminothiophene-2-acetonitrile As described under 3.1, 86 g (0.7 mol) of thiophene-2-acetonitrile are charged, with stirring and in the presence of 28 g (0.7 mol) of sodium hydroxide in 210 ml of methanol, with 0.7 mol of gaseous methyl nitrite at 0–5° C. over 4.5 hours. The ice bath is then removed and the brown solution is stirred overnight at room temperature. The solvent is distilled off and the residue is charged with water and toluene. The aqueous phase is separated, washed twice with ethyl acetate and acidified with conc. HCl. The aqueous phase is extracted twice with toluene, the extracts are washed with water and dried over magnesium sulfate. After filtration, the solvent is distilled off and the remaining brown solid is recrystallised from toluene, giving 28.6 g (39% of theory) of α-hydroxyiminothiophene-2-acetonitrile in the form of a beige solid having a melting point of 105–109° C. The $^1$H-NMR spectrum is consistent with the proposed structure.

Elemental analysis: $C_6H_4N_2OS$ (152.06)

|  | C [%] | H [%] | N [%] | S [%] |
|---|---|---|---|---|
| calcd.: | 47.36 | 2.65 | 18.41 | 21.07 |
| found: | 47.48 | 2.65 | 18.26 | 21.04 |

6.2 α-(Methylsulfonyloxyimino)thiophene-2-acetonitrile

In general analogy to the reaction described under 3.2, 38 g (0.25 mol) of α-hydroxyiminothiophene-2-acetonitrile and 37.95 g (0.375 mol) of triethylamine are dissolved in 350 ml of tetrahydrofuran and to this solution is then added dropwise a solution of 31.5 g (0.275 mol) of methanesulfonyl chloride at 0–5° C. After the addition is complete, the mixture is stirred for 30 minutes at 0° C. and then overnight at room temperature. The reaction mixture is filtered, the filtrate is washed with saturated sodium chloride solution and dried over magnesium sulfate. The solvent is distilled off on a rotary evaporator, giving a grey solid which is then recrystallised from toluene. 52.4 g (91%) of α-(methylsulfonyloxyimino)thiophene-2-acetonitrile are obtained in the form of beige crystals having an m.p. of 108–111° C. The $^1$H-NMR spectrum shows it to be a 55:45 mixture of the cis- and trans-isomers.

Elemental analysis: $C_7H_6N_2O_3S_2$ (230.26)

|  | C [%] | H [%] | N [%] | S [%] |
|---|---|---|---|---|
| calcd.: | 36.51 | 2.63 | 12.17 | 27.85 |
| found: | 36.89 | 2.60 | 12.22 | 28.23 |

EXAMPLES 7–11

The following Examples are prepared in general accordance with the procedure described in Example 5.2 by reacting α-hydroxyiminothiophene-2-acetonitrile with the corresponding sulfochlorides.

EXAMPLE 7

α-(Isopropylsulfonyloxyimino)thiophene-2-acetonitrile

Prepared by reacting α-hydroxyiminothiophene-2-acetonitrile with isopropylsulfonyl chloride. Recrystallisation gives a 60% yield of a 50:50 mixture of the cis- and trans-isomers ($^1$H-NMR analysis) of α-(isopropylsulfonyloxyimino)thiophene-2-acetonitrile in the form of beige crystals having an m.p. of 80–82° C. (Example 7a).

Elemental analysis: $C_9H_{10}N_2O_3S_2$ (258.31)

|  | C [%] | H [%] | N [%] | S [%] |
|---|---|---|---|---|
| calcd.: | 41.85 | 3.90 | 10.84 | 24.82 |
| found: | 41.89 | 3.93 | 10.76 | 24.84 |

Concentrating the mother liquor affords an additional 24% yield of a 25:75 mixture of the cis- and trans-isomers of the same substance, having an m.p. of 76–80° C. (Example 7b).

Elemental analysis: $C_9H_{10}N_2O_3S_2$ (258.31)

|        | C [%] | H [%] | N [%] | S [%] |
|--------|-------|-------|-------|-------|
| calcd.: | 41.85 | 3.90  | 10.84 | 24.82 |
| found:  | 42.13 | 3.90  | 10.55 | 25.01 |

EXAMPLE 8

α-(Butylsulfonyloxyimino)thiophene-2-acetonitrile

Prepared by reacting α-hydroxyiminothiophene-2-acetonitrile with butanesulfonyl chloride. Chromatography on silica gel gives a 90% yield of a 35:65 mixture of the cis- and trans-isomers ($^1$H-NMR analysis) of α-(butylsulfonyloxyimino)thiophene-2-acetonitrile in the form of a viscous reddish oil which solidifies to a resin upon standing.

Elemental analysis: $C_{10}H_{12}N_2O_3S_2$ (272.34)

|        | C [%] | H [%] | N [%] | S [%] |
|--------|-------|-------|-------|-------|
| calcd.: | 44.10 | 4.44  | 10.29 | 23.54 |
| found:  | 44.22 | 4.30  | 10.16 | 23.77 |

EXAMPLE 9

α-(Octylsulfonyloxyimino)thiophene-2-acetonitrile

Obtained by reacting α-hydroxyiminothiophene-2-acetonitrile with 1-octanesulfonyl chloride. Recrystallisation from toluene gives a 41% yield of a 78:22 mixture of the cis- and trans-isomers ($^1$H-NMR analysis) of α-(octylsulfonyloxyimino)thiophene-2-acetonitrile in the form of brownish crystals having an m.p. of 77–82° C. (Example 9a).

Elemental analysis: $C_{14}H_{20}N_2O_3S_2$ (328.44)

|        | C [%] | H [%] | N [%] | S [%] |
|--------|-------|-------|-------|-------|
| calcd.: | 51.20 | 6.14  | 8.53  | 19.52 |
| found:  | 50.94 | 6.10  | 8.56  | 19.56 |

Concentrating the mother liquor affords an additional 44% yield of a 33:67 mixture of the cis- and trans-isomers of the same substance, having an m.p. of 48–55° C. (Example 9b).

Elemental analysis: $C_{14}H_{20}N_2O_3S_2$ (328.44)

|        | C [%] | H [%] | N [%] | S [%] |
|--------|-------|-------|-------|-------|
| calcd.: | 51.20 | 6.14  | 8.53  | 19.52 |
| found:  | 51.47 | 6.05  | 8.31  | 19.45 |

EXAMPLE 10

α-(Dodecylsulfonyloxyimino)thiophene-2-acetonitrile

Prepared by reacting α-hydroxyiminothiophene-2-acetonitrile with dodecanesulfonyl chloride. Recrystallisation from toluene gives a 41% yield of a 90:10 mixture of the cis- and trans-isomers ($^1$H-NMR analysis) of α-(dodecylsulfonyloxyimino)thiophene-2-acetonitrile in the form of brownish crystals having an m.p. of 94.5–97° C. (Example 10a).

Elemental analysis: $C_{18}H_{28}N_2O_3S_2$ (384.55)

|        | C [%] | H [%] | N [%] | S [%] |
|--------|-------|-------|-------|-------|
| calcd.: | 56.22 | 7.34  | 7.28  | 16.67 |
| found:  | 55.95 | 7.23  | 7.54  | 16.72 |

Concentration of the mother liquor and column chromatography thereof (silica gel, eluant: petroleum th r/ethyl acetat 5:1) gives an additional 11% yield of a 20:80 mixture of the cis- and trans-isomers of the same substance, having an m.p. of 66–69° C. (Example 10b).

Elemental analysis: $C_{18}H_{28}N_2O_3S_2$ (384.55)

|        | C [%] | H [%] | N [%] | S [%] |
|--------|-------|-------|-------|-------|
| calcd.: | 56.22 | 7.34  | 7.28  | 16.67 |
| found:  | 57.39 | 7.71  | 6.65  | 15.58 |

EXAMPLE 11

α-(3-Chloropropylsulfonyloxyimino)thiophene-2-acetonitrile

Prepared by reacting α-hydroxyiminothiophene-2-acetonitrile with 3-chloropropane sulfonyl chloride. Chromatography on silica gel gives a 90% yield of a 60:40 mixture of the cis- and trans-isomers ($^1$H-NMR analysis) of α-(3-chloropropylsulfonyloxyimino)thiophene-2-acetonitrile in the form of a resin which solidifies upon standing. M.p.=56–58° C.

Elemental analysis: $C_9H_9ClN_2O_3S_2$ (292.76)

|        | C [%] | H [%] | N [%] | S [%] |
|--------|-------|-------|-------|-------|
| calcd.: | 36.92 | 3.10  | 9.57  | 21.90 |
| found:  | 36.71 | 3.19  | 9.20  | 21.99 |

EXAMPLE 12

α-(Trifluorometyhlsulfonyloxyimino)thiophene-2-acetonitrile 10 g (0.065 mol) of α-hydroxyiminothiophene-2-acetonitrile are suspended in 100 ml of dichloromethane and then 5.2 g (0.065 mol) of pyridine are added. To this suspension is then added dropwise a solution of 19.5 g (0.07 mol) of trifluoromethanoic acid anhydride at −30 to −20° C. After the addition is complete, the mixture is stirred for one hour at −20° C. and then overnight at room temperature. Subsequently, the reaction mixture is poured on ice/water, the aqueous phase is extracted with dichloromethane and the combined organic phases are dried over magnesium sulfate. The crude product is filtered over silica gel (eluant: ethyl acetate) and the solution is concentrated and stored at 0–5° C. After some time, 5 g (26%) of α-(trifluorometyhlsulfonyloxyimino)thiophene-2-acetonitrile precipitate in the form of brownish crystals having an m.p. of 47–48° C. The $^1$H-NMR spectrum shows it to be a 1:1 mixture of the cis- and trans-isomers.

Elemental analysis: $C_7H_3F_3N_2O_3S_2$ (284.23)

|  | C [%] | H [%] | N [%] | S [%] |
|---|---|---|---|---|
| calcd.: | 29.59 | 1.06 | 9.86 | 22.56 |
| found: | 29.92 | 1.11 | 9.89 | 22.61 |

EXAMPLES 13–14

The following Examples are prepared in general accordance with the procedure of Example 1.2 by reacting α-hydroxyimino-4-methoxybenzylcyanide with the corresponding sulfochlorides.

EXAMPLE 13

α-(Octylsulfonyloxyimino)-4-methoxybenzylcyanide

Obtained by reacting α-hydroxyimino-4-methoxybenzylcyanide with 1-octane sulfonyl chloride. Chromatography on silica gel (eluant: hexane:ethyl acetate 4:1) gives a 77% yield of a 63:37 mixture of the cis- and trans-isomers ($^1$H-NMR analysis) of α-(octylsulfonyloxyimino)-4-methoxybenzylcyanide in the form of an yellowish-orange viscous oil.

Elemental analysis: $C_{17}H_{24}N_2O_4S$ (352.45)

|  | C [%] | H [%] | N [%] | S [%] |
|---|---|---|---|---|
| calcd.: | 57.93 | 6.86 | 7.95 | 9.10 |
| found: | 58.19 | 7.02 | 7.69 | 8.90 |

EXAMPLE 14

α-(3-Chloropropylsulfonyloxyimino)-4-methoxybenzylcyanide

Prepared by reacting α-hydroxyimino-4-methoxybenzylcyanide with 3-chloropropane sulfonyl chloride. Chromatography on silica gel (eluant hexane:ethyl acetate 4:1) gives a 50% yield of a 58:42 mixture of the cis- and trans-isomers ($^1$H-NMR analysis) of α-(3-chloropropylsulfonyloxyimino)4-methoxybenzylcyanide in the form of a yellowish-orange viscous oil (Example 14a).

Elemental analysis: $C_{12}H_{13}ClN_2O_4S$ (316.76)

|  | C [%] | H [%] | N [%] | S [%] |
|---|---|---|---|---|
| calcd.: | 45.50 | 4.14 | 8.84 | 10.12 |
| found: | 46.21 | 4.02 | 9.52 | 9.93 |

A second chromatographic fraction affords an additional 7% yield of a 87:13 mixture of the cis- and trans-isomers ($^1$H-NMR analysis) of α-(3-chloropropylsulfonyloxyimino)-4-methoxy-benzylcyanide in the form of a yellowish viscous oil (Example 14b).

Elemental analysis: $C_{12}H_{13}ClN_2O_4S$ (316.76)

|  | C [%] | H [%] | N [%] | S [%] |
|---|---|---|---|---|
| calcd.: | 45.50 | 4.14 | 8.84 | 10.12 |
| found: | 45.82 | 4.11 | 9.08 | 9.97 |

EXAMPLE 15

Preparation of a Photoresist

65 Parts of polyvinyl phenol (Mw=4000, Maruzen Chemicals), 30 parts of hexa(methoxy-methyl)melamine (Cymel®303, Cyanamid) and 5 parts of the compound to be tested are mixed. 2.5 g of this mixture are dissolved in 7.5 g of 1-methoxy-2-propylacetate which comprises 1000 ppm of a flow control agent (FC430). This solution is applied by spin coating for 30 s at 5000 rev/min to the polished and hexamethyldisilazane-treated side of silicon wafers having a diameter of 10.2 cm (4 inches). This results in a 1 μm coating thickness. The solvent is removed by drying the coated wafer on a hotplate at 110° C. for 60 seconds, giving a film of about 1 μm. The samples thus obtained are irradiated image-wise through a mask with areas of different grey scales, using interference filters that are selectively permeable to light of wavelengths of 365 nm (Canon PLA 501, mercury high-pressure lamp). The samples are then heated to 110° C. for 60 seconds in order to effect crosslinking in the irradiated areas, catalysed by the acid generated by the irradiation. Developing is then carried out for 60 seconds in a 238% solution of tetramethylammonium hydroxide. The radiation dose that is required to achieve a film thickness after developing that corresponds to the thickness before developing is then determined. The measurement of the film thickness is carried out using a Zeiss Axiotron (white-light interference). The lower the radiation dose required, the more reactive is the latent photohardener. The results are listed in Table 1. They show that using the photohardeners of this invention gives negative resists of high sensitivity.

TABLE 1

| Photohardener of Example | Sensitivity at 365 nm [mJ/cm$^2$] |
|---|---|
| 1 | 13 |
| 2 | 14 |
| 6 | 40 |
| 7a | 40 |
| 8 | 45 |
| 9a | 30 |
| 10a | 50 |
| 11 | 50 |
| 13 | 15 |
| 14a | 15 |

EXAMPLE 16

Preparation of Positive Resists

16a: The Preparation of the Binder Polymer is Carried Out in General Analogy to U. Schädeli et al. U.S. Pat. No. 5,558,978 (1996): Terpolymer Consisting of tetrahydro-2H-pyranyloxy-styrene, N, hydroxymethyl maleinimide and N-acetoxymethyl maleinimide: In a 1000 ml round bottomed flask, a solution of 56.29 g (276 mmol) of tetrahydro-2H-pyranyloxystyrene, 8.76 g (58 mmol) of N-hydroxymethylmaleinimide, 35.00 g (207 mmol) of N-acetoxymethlmaleinimide and 4.0 g of dibenzoylperoxide in 400 ml of tetrahydrofuran is stirred for 4 hour under a nitrogen atmosphere at 60° C. The reaction solution is cooled and then precipitated from 2 liters of methanol. The precipitate that forms is filtered off and dried under vacuum (20 mbar), giving 88.1 g (88% of theory) of a white powder.

GPC (poylstyrene calibration ): Mn=10 600, Mw=67 800, PD=6.4 TGA (10° C./min): weight loss of 25% between 170–250° C.

16b: Preparation of Positive i-line Resists 16b.1: A resist solution is prepared by dissolving 0.98 g of the polymer of Example 16a and 20 mg of the photoinitiators of Example 1 in 6 g of 1-methoxy-2-propylacetate. This solution is applied by spin coating at 1300 rev/min to a silicon wafer having a diameter of 3 inches. Subsequent drying at 100° C. for 1 min results in a film having a 1.1 micrometer coating thickness. Using a mercury vapour lamp of the Ushio UXM-502 MD type, this film is irradiated image-wise through a narrow band interference filter and a chromium/quartz mask at 365 nm at a dose of 36 mJ/cm². The wafer is then heated on a hotplate for one minute to 100° C. and then developed in a 0.262 N solution of tetramethylammonium hydroxide in water, the previously irradiated zones of the resist film dissolving, but the non-irradiated zones remaining. Positive images of the mask are obtained having good resolution.

16.b.2: A resist solution is prepared by dissolving 0.98 g of the polymer of Example 16a and 20 mg of the photoinitiator of Example 2 in 6 g of 1-methoxy-2-propylacetate. This solution is applied by spin coating at 1300 rev/min to a 3 inch silicon wafer. Subsequent drying at 100° C. for 1 min gives a film having a coating thickness of 1.1 micrometer. Using a mercury vapour lamp of the Ushio UXM-502 MD type, this film is irradiated image-wise through a narrow band interference filter and a chromium/quartz mask at 365 nm at a dose of 32 mJ/cm². The wafer is then heated on a hotplate for one minute to 100° C. and then developed in a 0.262 N solution of tetramethylammonium hydroxide in water, the previously irradiated zones of the resist film dissolving, but the non-irradiated zones remaining. Positive images of the mask are obtained having good resolution.

16.b.3: A resists solution is prepared by dissolving 0.98 g of the polymer of Example 16a and 20 mg of the photoinitiator of Example 6 in 6 g of 1-methoxy-2-propylacetate. This solution is applied by spin coating at 1300 rev/min to a 3 inch silicon wafer. Subsequent drying at 100° C. for 1 min results in a film having a 1.1 micrometer coating thickness. Using a mercury vapour lamp of the Ushio UXM-502 MD type, this film is irradiated image-wise through a narrow band interference filter and a chromium/quartz mask at 365 nm at a dose of 72 mJ/cm². The wafer is then heated on a hotplate for one minute to 100° C. and then developed in a 0.262 N solution of tetramethylammonium hydroxide in water, the previously irradiated zones of the resist film dissolving, but the non-irradiated zones remaining. Positive patterns of the mask are obtained having good resolution.

What is claimed is:

1. A compound of formula 1a

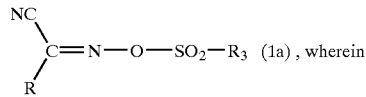

-continued

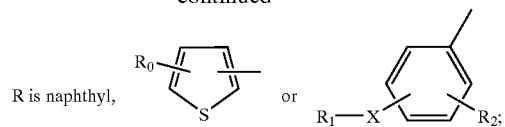

$R_0$ is either a $R_1$—X group or $R_2$;

X is a direct bond, an oxygen atom or a sulfur atom;

$R_1$ is hydrogen, $C_1$–$C_4$alkyl or a phenyl group which is unsubstituted or substituted by a substituent selected from the group consisting of chloro, bromo, $C_1$–$C_4$alkyl and $C_1$–$C_4$-alkyloxy;

$R_2$ is hydrogen or $C_1$–$C_4$alkyl; and $R_3$ is octyl or dodecyl.

2. A compound according to claim 1, which is selected from the group consisting of α-(octylsulfonyloxyimino) thiophene-2-acetonitrile, α-(dodecylsulfonyloxyimino) thiophene-2-acetonitrile and α-(octylsulfonyloxyimino)-4-methoxybenzyl cyanide.

3. A composition which can be activated by light, comprising a) at least one compound which may be crosslinked by the action of an acid and/or b) at least one compound which changes its solubility under the action of an acid, and c) as photoinitiator at least one compound of formula 1

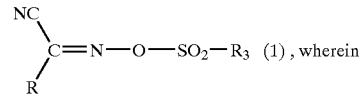

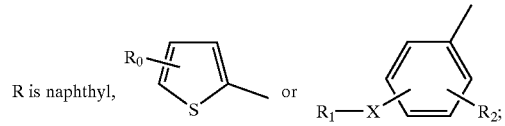

$R_0$ is either an $R_1$—X group or $R_2$;

X is a direct bond or an oxygen atom;

$R_1$ is hydrogen, $C_1$–$C_4$alkyl which is unsubstituted or substituted by phenyl, OH or $C_{1-4}$-alkoxy or which may be interrupted by an —O-atom, or $R_1$ is a phenyl group which is unsubstituted or substituted by a substituent selected from the group consisting of chloro, bromo, $C_1$–$C_4$alkyl and $C_1$–$C_4$alkyloxy;

$R_2$ is hydrogen or $C_1$–$C_4$alkyl; and $R_3$ is octyl or dodecyl.

4. A composition according to claim 3, wherein the photoinitiator is selected from the group consisting of α-(octylsulfonyloxyimino)thiophene-2-acetonitrile, α-(dodecylsulfonyloxyimino)thiophene-2-acetonitrile and α-(octylsulfonyloxyimino)-4-methoxybenzyl cyanide.

5. A chemically amplified positive photoresist which is developable in alkaline medium and which is sensitive to radiation in the wavelength from 340 to 390 nanometers, which resist is based on oxime alkyl sulfonates as photosensitive acid generator and contains a compound of formula 1

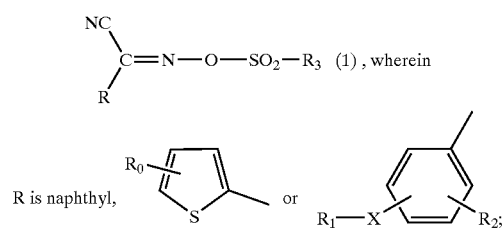

R is naphthyl, $R_0$ is either an $R_1$—X group or $R_2$;
X is a direct bond or an oxygen atom;
$R_1$ is hydrogen, $C_1$–$C_4$alkyl which is unsubstituted or substituted by phenyl, OH or $C_1$–$C_4$-alkoxy or which may be interrupted by an —O-atom, or $R_1$ is a phenyl group which is unsubstituted or substituted by a substituent selected from the group consisting of chloro, bromo, $C_1$–$C_4$alkyl and $C_1$–$C_4$alkyloxy;
$R_2$ is hydrogen or $C_1$–$C_4$alkyl; and
$R_3$ is octyl or dodecyl;
as at least one of said oxime alkyl sulfonates.

6. A chemically amplified positive photoresist according to claim 5 wherein the compound of formula 1 is selected from the group consisting of α-(octylsulfonyloxyimino)thiophene-2-acetonitrile, α-(dodecylsulfonyloxyimino)thiophene-2-acetonitrile and α-(octylsulfonyloxyimino)-4-methoxybenzyl cyanide.

7. A chemically amplified negative photoresist which is developable in alkaline medium and which is sensitive to radiation in the wavelength from 340 to 390 nanometers, which resist is based on oxime alkyl sulfonates as photosensitive acid generator and contains a compound of formula 1

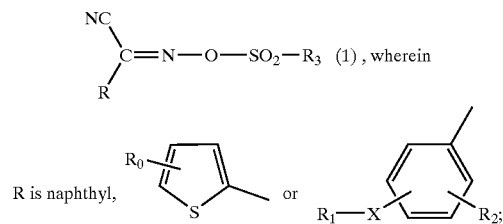

R is naphthyl, $R_0$ is either an $R_1$—X group or $R_2$;
X is a direct bond or an oxygen atom;
$R_1$ is hydrogen, $C_1$–$C_4$alkyl which is unsubstituted or substituted by phenyl, OH or $C_1$–$C_4$-alkoxy or which may be interrupted by an —O-atom, or $R_1$ is a phenyl group which is unsubstituted or substituted by a substituent selected from the group consisting of chloro, bromo, $C_1$–$C_4$alkyl and $C_1$–$C_4$alkyloxy;
$R_2$ is hydrogen or $C_1$–$C_4$alkyl; and
$R_3$ is octyl or dodecyl;
as at least one of said oxime alkyl sulfonates.

8. A chemically amplified negative photoresist according to claim 7 wherein the compound of formula 1 is selected from the group consisting of α-(octylsulfonyloxyimino)thiophene-2-acetonitrile, α-(dodecylsulfonyloxyimino)thiophene-2-acetonitrile and α-(octylsulfonyloxyimino)-4-methoxybenzyl cyanide.

9. A process for the production of images, which comprises coating a substrate with a composition comprising
a) at least one compound which may be crosslinked by the action of an acid and/or b) at least one compound which changes its solubility under the action of an acid, and
c) as photoinitiator at least one compound of formula 1

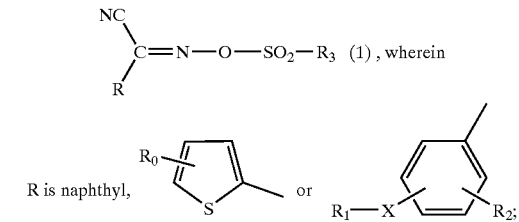

R is naphthyl, $R_0$ is either an $R_1$—X group or $R_2$;
X is a direct bond or an oxygen atom;
$R_1$ is hydrogen, $C_1$–$C_4$alkyl which is unsubstituted or substituted by phenyl, OH or $C_1$–$C_4$-alkoxy or which may be interrupted by an —O-atom, or $R_1$ is a phenyl group which is unsubstituted or substituted by a substituent selected from the group consisting of chloro, bromo, $C_1$–$C_4$alkyl and $C_1$–$C_4$alkyloxy;
$R_2$ is hydrogen or $C_1$–$C_4$alkyl; and
$R_3$ is octyl or dodecyl;
irradiating the coating with radiation having a wavelength of 340 to 390 nanometers in a desired pattern and, after a heating period, removing the more soluble parts of the coating with an aqueous-alkaline developer.

10. A process according to claim 9 for the production of images, wherein the compound of formula 1 is selected from the group consisting of α-(octylsulfonyloxyimino)thiophene-2-acetonitrile, α-(dodecylsulfonyloxyimino)thiophene-2-acetonitrile and α-(octylsulfonyloxyimino)-4-methoxybenzyl cyanide.

11. A process for generating acids in a photoresist sensitive to radiation at a wavelength of up to 390 nanometers which comprises adding an oxime alkyl sulfonate compound of formula 1

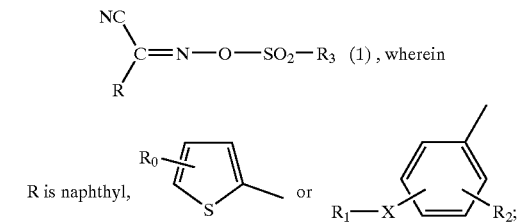

R is naphthyl, $R_0$ is either an $R_1$—X group or $R_2$;
X is a direct bond or an oxygen atom;
$R_1$ is hydrogen, $C_1$–$C_4$alkyl which is unsubstituted or substituted by phenyl, OH or $C_1$–$C_4$-alkoxy or which may be interrupted by an —O-atom, or $R_1$ is a phenyl group which is unsubstituted or substituted by a substituent selected from the group consisting of chloro, bromo, $C_1$–$C_4$alkyl and $C_1$–$C_4$alkyloxy;
$R_2$ is hydrogen or $C_1$–$C_4$alkyl; and
$R_3$ is octyl or dodecyl;
as photosensitive acid generator and irradiating with radiation at a wavelength of up to 390 nanometers.

12. A process for generating acids in a photoresist sensitive to radiation at a wavelength of up to 390 nanometers according to claim 11 wherein the oxime alkyl sulfonate compound of formula 1 is selected from the group consisting of α-(octylsulfonyloxyimino)thiophene-2-acetonitrile, α-(dodecylsulfonyloxyimino)thiophene-2-acetonitrile and α-(octylsulfonyloxyimino)-4-methoxybenzyl cyanide.

13. A process for the production of printing plates, color filters, resist materials and image recording materials, wherein a composition comprising
   a) at least one compound which may be crosslinked by the action of an acid and/or
   b) at least one compound which changes its solubility under the action of an acid, and
   c) as photoinitiator at least one compound of formula (1)

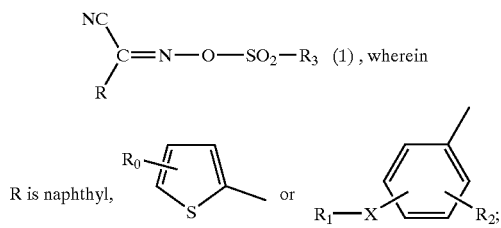

R is naphthyl, $R_0$ is either an $R_1$—X group or $R_2$;

X is a direct bond or an oxygen atom;

$R_1$ is hydrogen, $C_1$–$C_4$alkyl which is unsubstituted or substituted by phenyl, OH or $C_1$–$C_4$-alkoxy or which may be interrupted by an —O-atom, or $R_1$ is a phenyl group which is unsubstituted or substituted by a substituent selected from the group consisting of chloro, bromo, $C_1$–$C_4$alkyl and $C_1$–$C_4$alkyloxy;

$R_2$ is hydrogen or $C_1$–$C_4$alkyl; and $R_3$ is octyl or dodecyl, is irradiated with radiation at a wavelength of up to 390 nanometers.

14. A process for the production of printing plates, color filters, resist materials and image recording materials according to claim 13, wherein the compound of formula 1 is selected from the group consisting of α-(octylsulfonyloxyimino)thiophene-2-acetonitrile, α-(dodecylsulfonyloxyimino)thiophene-2-acetonitrile and α-(octylsulfonyloxyimino)-4-methoxybenzyl cyanide.

* * * * *